United States Patent

Hofen et al.

[11] Patent Number: 5,886,230
[45] Date of Patent: Mar. 23, 1999

[54] PROCESS FOR CONTINUOUS PRODUCTION OF METHYL MERCAPTAN

[75] Inventors: Willi Hofen, Rodenbach; Wolfgang Boeck, Langenselbold; Stephan Rautenberg, Hanau; Joerg Sauer, Rodenbach; Dietrich Arntz, Oberursel; Ralf Goedecke, Rodenbach; Wolfgang Taugner, Altenstadt; Raymund Sonnenschein, Alzenau, all of Germany

[73] Assignee: Degussa Aktiengesellschaft, Frankfurt am Main, Germany

[21] Appl. No.: 885,044

[22] Filed: Jun. 30, 1997

[30] Foreign Application Priority Data

Dec. 27, 1996 [DE] Germany ............... 196 54 515.3

[51] Int. Cl.[6] ............................................ C07C 319/00
[52] U.S. Cl. ........................................................ 568/71
[58] Field of Search .................................................. 568/71

[56] References Cited

U.S. PATENT DOCUMENTS 2,822,401  2/1958  Hoot et al. ............................. 568/71
3,935,276  1/1976  Biola et al. ............................ 568/71

FOREIGN PATENT DOCUMENTS 2477538   9/1981  France .
1134368   8/1962  Germany .
17686826  8/1971  Germany .
810017    3/1959  United Kingdom .

Primary Examiner—Gary Geist
Assistant Examiner—Jafar Parsa
Attorney, Agent, or Firm—Beveridge, DeGrandi, Weilacher & Young, L.L.P.

[57] ABSTRACT

A process for continuous production of methyl mercaptan by catalytic reaction of methanol and hydrogen sulfide. Significant improvements in the pretreatment of the feed gas mixture and in utilization of the heat of reaction and the heat content of the product gas mixture. The energy required to vaporize the methanol is derived partly from utilization of the heat of compression of the hydrogen sulfide gas and from the heat content of the product gas leaving the reactor. The heat of reaction is utilized to heat the feed gas mixture to the reaction temperature, with the help of an external gas heater.

6 Claims, 2 Drawing Sheets

5,886,230

PROCESS FOR CONTINUOUS PRODUCTION OF METHYL MERCAPTAN

INTRODUCTION AND BACKGROUND

The present invention relates to a process for continuous production of methyl mercaptan by reacting an educt gas mixture of methanol and hydrogen sulfide in the vapor phase at a reaction temperature between 300° C. and 500° C. and under an operating pressure of 5 to 15 bar over a catalyst bed containing aluminum oxide, with subsequent separation of the methyl mercaptan from the gas mixture by absorption and distillation, with recycling of the unconsumed methanol and hydrogen sulfide, as well as removal of inert gases and waste water and replacement of consumed methanol and hydrogen sulfide.

Methyl mercaptan is an important industrial intermediate for synthesis of methionine and for production of dimethyl sulfoxide and dimethyl sulfone. At present it is produced predominantly from methanol and hydrogen sulfide by reaction at an aluminum oxide catalyst. Methyl mercaptan is usually synthesized in the gas phase at temperatures between 300° C. and 500° C. and at pressures between 1 and 25 bar. The catalyst is usually doped with potassium tungstate as an activator to increase its activity and selectivity. The reaction of hydrogen sulfide and methanol to produce methyl mercaptan is an exothermic process which releases 28,500 kJ per kmol methanol reacted.

The product gas mixture resulting from this known process contains not only the methyl mercaptan and water which are formed but also the unreacted starting materials, methanol and hydrogen sulfide, the byproducts dimethyl sulfide and dimethyl ether, and small proportions of polysulfides. The product gas mixture also contains gases which are inert in this reaction: carbon dioxide, carbon monoxide, nitrogen and hydrogen.

The methyl mercaptan produced is separated from the product gas mixture in several distillation and washing columns at temperatures between 10° C. and 140° C., as shown in German Patent 17 68 826. Other product streams contain excess hydrogen sulfide, methanol, the inert gases, and wastewater. Methanol is used preferably as the washing liquid.

Excess hydrogen sulfide is returned to the pressurized reactor as "recycled gas". The recycled gas contains not only hydrogen sulfide but also methanol, methyl mercaptan, dimethyl sulfide, and other components of the product gas mixture. The proportion of these components in the recycled gas depends on the quality of the separation process. The unconsumed methanol is also recycled into the feed gas mixture. The recycled methanol, like the recycled gas, also contains other components. The hydrogen sulfide and methanol that are consumed are replaced by adding fresh materials.

The overall process of methyl mercaptan production can be divided into two parts. The first part includes pretreatment of the feed gas mixture and its conversion to methyl mercaptan. The second part includes the separation of the product gas mixture to recover methyl mercaptan, recycling of unconsumed methanol and hydrogen sulfide, and disposal of wastewater and waste gases. This invention is concerned with improvements in the first part of the production process.

The nature of the pretreatment of the feed gas mixture, its heating to the reaction temperature, and the subsequent cooling of the product gas mixture to condense and separate the methyl mercaptan have substantial effects on the economics of the overall process. High electrical power is required to operate the compressor, and large heating and cooling capacities are needed.

German Patent 17 68 826 has very little information about this first part of the production process. It can be seen from the process schematically presented that the recycled gas, together with the hydrogen sulfide make-up gas, is heated by the hot product gas mixture in a heat exchanger. The product gas mixture is cooled at the same time. The methanol required for the reaction is mixed into the hydrogen sulfide to produce the feed gas mixture after the hydrogen sulfide has been heated in the heat exchanger, shortly before entry into the reactor. The methanol washed from the product gas mixture is removed from the circulating wash liquid for that purpose. The amount removed from the circulating liquid is replaced with make-up methanol.

According to French Patent 2 477 538, make-up hydrogen sulfide gas for methyl mercaptan production is compressed in a compressor to 11 bar. Then recycle gas from the process, which contains hydrogen sulfide, dimethyl sulfide, methanol, and small proportions of methyl mercaptan is added to the compressed hydrogen sulfide to produce the feed gas mixture. The temperature of the feed gas mixture is raised to 510° C. in a preheating furnace. circulating wash liquid, which contains methanol and dimethyl sulfide, is added to the feed gas mixture before it enters the first of up to ten reactors connected in cascade. That reduces the reactor inlet temperature to 450° C. More methanol is injected into the gas stream, partly as liquid and partly as gas, before the second and subsequent reactors. All or part of the heat released in the reaction can be absorbed by the heat of vaporization needed for the methanol.

German Patent 11 34 368 describes use of a multitude reactor to produce methyl mercaptan. The multitude reactor comprises a cylindrical container in which the catalyst tubes are arranged parallel with each other. The catalyst tubes are welded to tube sheets at the top and bottom, as in multitude heat exchangers. The spaces between the tubes are filled with heat-transfer liquid. Each catalyst tube has, for example, a screen at its lower end which holds the particulate catalyst. The feed gas mixture flows upward through the reactor.

The catalyst comprises activated aluminum oxide in the form of spherical particles of mesh size 8 to 14. It is preferable for the catalyst to be diluted with inert material, such as silica or fused aluminum oxide, in the lower section of the catalyst tubes, so that the inert materials make up about 75% of the particles in the lower third of the tubes. The proportion of inert material decreases from this height up to the upper section of the tubes, so that there is pure catalyst in the upper part of the tubes. The gradually reduced dilution of the catalyst in the direction of flow gives a more even evolution of heat, which simplifies temperature control.

German Patent 11 34 368 uses a eutectic mixture of diphenyl ether and diphenyl as the heat-transfer liquid. This cooling liquid is vaporized by the heat of reaction, and is condensed into a coolant tank and returned to the reactor. According to German Patent 11 34 368 the feed gas mixture is heated by heat exchange with the hot product gas mixture and the hot coolant vapors.

An object of this invention is to improve the process for producing methyl mercaptan and an enhancement of the economics of the overall process, with respect to both the capital cost and the operating power costs, through improved pretreatment of the feed gas mixture and better utilization of the reaction heat.

SUMMARY OF THE INVENTION

The above and other objects of the invention are achieved by a process for continuous production of methyl mercaptan wherein a specially prepared feed gas mixture of methanol and hydrogen sulfide are reacted in the vapor phase at a reaction temperature between 300° C. to 500° C. and under an operating pressure of 5 to 15 bar in a catalyst bed containing aluminum oxide. More particular, the claimed process features the fact that the feed gas mixture is obtained by the following process steps:

a) compression of hydrogen sulfide make-up gas to an intermediate pressure with addition of liquid methanol, b) mixing recycled hydrogen sulfide gas to the make-up gas and compression of the mixture to the operating pressure, c) addition of supplemental methanol in the form of methanol vapor to the compressed gas mixture to produce a feed gas mixture having a molar ratio of hydrogen sulfide to methanol of 1.1 to 3, d) heating the feed gas mixture to a preheat temperature in the range of 150° C. to 200° C., e) further heating of the feed gas mixture to the reaction temperature in heat exchange with the reaction heat released in the catalyst bed, and f) reaction of methanol and hydrogen sulfide to produce methyl mercaptan in the catalyst bed.

BRIEF DESCRIPTION OF DRAWINGS

The present invention will be further understood with reference to the drawings, wherein.

DETAILED DESCRIPTION OF THE INVENTION

Figure 1:
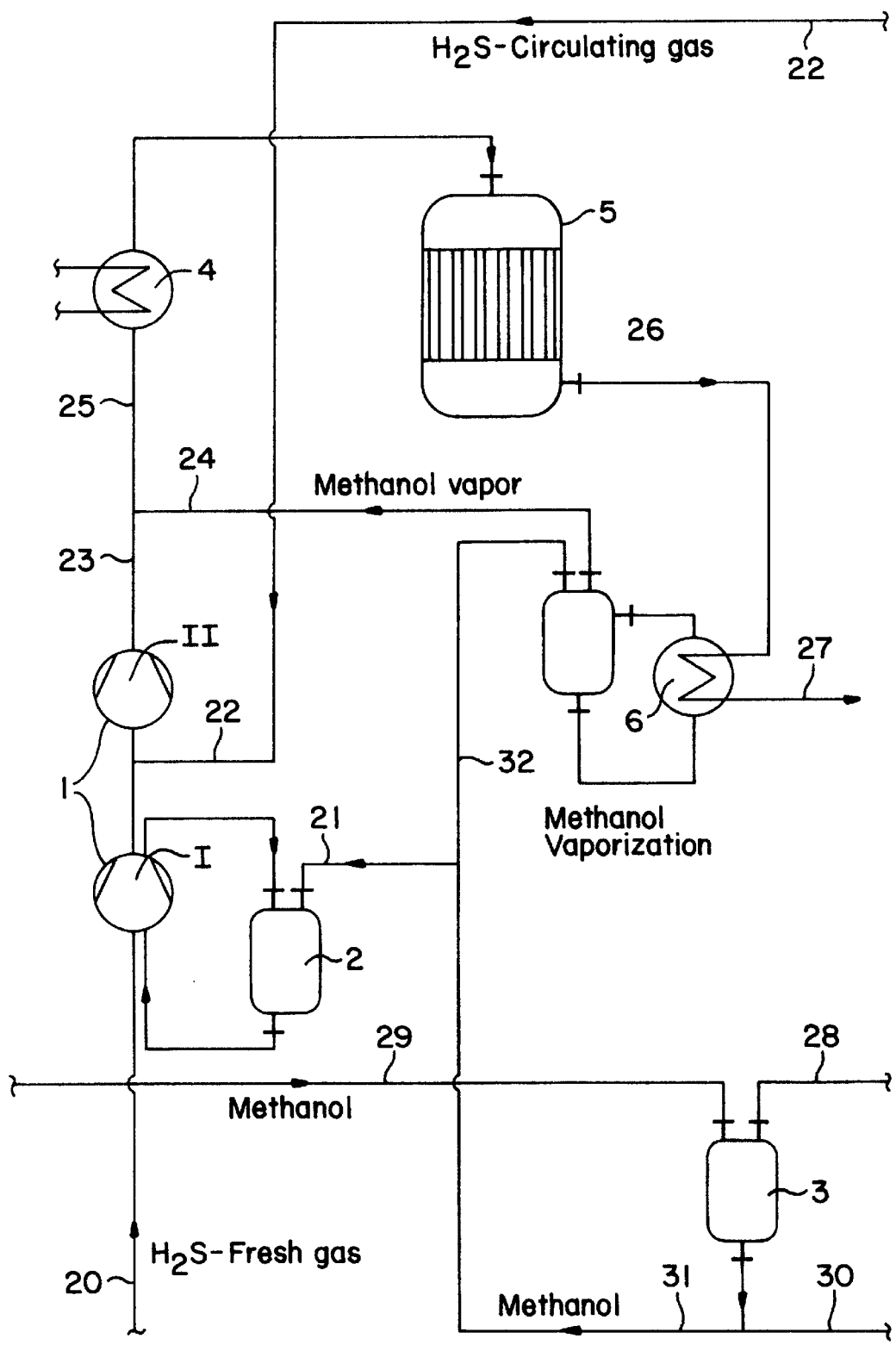
FIG. 1 is a flow diagram for the first part of the process of producing methyl mercaptan according to the present invention.

According to the present invention, the hydrogen sulfide make-up gas is first compressed from normal pressure to an intermediate pressure in an initial compression step. In the process, liquid methanol is added by spraying or injection before or during the compression process. The heat of compression released in the compression partially vaporizes the methanol. In this way, the temperature rise of the compressed gas can be limited to less than 100° C. After the compression, the gas flow is saturated with methanol at the temperature prevailing after the first compression stage.

The hydrogen sulfide gas separated from the product gas mixture and recirculated, called "recycled gas" in the following, along with the precompressed make-up gas, is compressed from the intermediate pressure to the operating pressure in a second compression stage. Because of the limitation of the temperature in the first compression stage, the gas temperatures rises only to a maximum of 140° C. after the second compression stage.

Because methanol is injected in the first compression, stage, part of the compression energy is utilized to vaporize methanol, simultaneously limiting the temperature in the first compression stage. That avoids capital costs for an intercooler which would otherwise be needed, and also avoids operating costs for cooling water. Other savings arise from the fact that part of the methanol needed for the reaction is vaporized by the heat produced by compression.

After the first compression stage, more methanol is added to the feed gas in the form of methanol vapor to adjust the molar ratio of hydrogen sulfide to methanol to a value of 1.1 to 3.

A high molar ratio favors the catalytic conversion of hydrogen sulfide and methanol to methyl mercaptan. Of course, a. large excess of hydrogen sulfide means that large volumes of hydrogen sulfide must be recirculated. Therefore the molar ratio should not exceed 3 to limit the power cost of recirculation. With values below 1.1, on the other hand, the conversion to methyl mercaptan is unsatisfactory, even if highly active and selective catalysts are used. Therefore it is preferable to establish a molar ratio of 1.5 to 2.0.

The proportion of the methanol that can be vaporized in the first compression stage depends on the intermediate pressure and the molar ratio selected. The higher the molar ratio, the more hydrogen sulfide must be compressed, relative to the methanol, so that more methanol can be vaporized. It is preferable to select an intermediate pressure about half the working pressure. In this case, for example, at a molar ratio of 1.8 and an intermediate pressure of 6 bar, about 25% of the total methanol needed for the reaction can be vaporized in the first stage.

The temperature of the feed gas mixture obtained in this manner is raised to a preheat temperature in the range between 150° C. and 200° C. by adding external heat with a gas heater before it is heated to the actual working temperature by heat exchange with the reaction heat liberated in the catalyst bed and is passed over the catalyst bed for conversion of hydrogen sulfide and methanol to methyl mercaptan.

In one preferred embodiment of the invention, the catalytic reaction is carried out in a multitude reactor. Its tubes are filled, in the direction of flow, first with an inert packing and then with the catalyst packing, so that the reaction heat liberated in the catalyst packing is transferred, by means of a heat-transfer medium circulating between the tubes, to the upstream inert packing to heat the feed gas mixture to the reaction temperature. That is done by pumping the heat transfer medium through the reactor shell in countercurrent flow to the flow of the feed gas mixture, so that the reaction heat liberated in the catalyst packing is transferred to the inert filling. For example, a molten salt is suitable as a heat-transfer medium. The lengths of the inert filling and catalyst filling, as well as the preheat temperature (reactor inlet temperature) can be matched to each other in a simple manner so that the feed gas mixture is heated to the reaction temperature of 300° C. to 500° C. after passing through the inert filling.

This manner of operating the reactor offers many advantages. For instance, the external gas heater need only heat the feed gas mixture to 200° C. at the highest, so that it is correspondingly simple to design. By contrast, the feed gas mixture in French Patent 2 477 538 must be heated to 510° C. before it enters the reactor. That requires an expensive gas heater with large heating capacity. It must be made of corrosion-resistant materials, because, as is well known, hydrogen sulfide is severely corrosive at temperatures above 500° C.

Because of the internal heat exchange in the reactor, measures for removing the heat of reaction are not needed. The systems for heating and cooling the circulating heat-transfer medium, needed for temperature control of the reactor, can be designed correspondingly small. On the other hand, according to German Patent 11 34 368, the entire heat of reaction must be transferred outward by the coolant and transferred to the feed gas mixture in a separate heat exchanger.

In another preferred embodiment of the invention, the energy required to vaporize the methanol is removed from the product gas mixture with a heat exchanger after it leaves the pressurized reactor. In this process, the product gas mixture is cooled to 100° C. to 150° C. The enthalpy of the product gas mixture, up to 150° C., is adequate to vaporize all the methanol needed in the process; for example, at a temperature of 137° C. and 10 bar. Coupling the methanol vaporization to the heat of reaction essentially establishes automatically the molar ratio of hydrogen sulfide to methanol required for the reaction.

Separation of the compression of the feed gas to the operating pressure in two stages is preferably done with a two-stage compressor, in which the gas mixture is compressed to the intermediate pressure in the first stage and to the working pressure in the second stage. Two-stage screw-type compressors are particularly suitable. These compressors are very compact and robust. The methanol can be injected directly into the first compression stage. In this process it has proven advantageous to inject methanol in excess; that is, to add more methanol than can be vaporized by the heat of compression. The excess methanol, which is not evaporated, is separated at the output of the first compressor stage and returned to the input. This portion of circulating liquid methanol flushes the first compressor stage, removing coarse sulfur deposits. The particles suspended in the methanol are separated in a filter. The ratio of vaporized to non-vaporized methanol can be varied within wide limits. A weight ratio of 2:1 has proved good.

Figure 2:
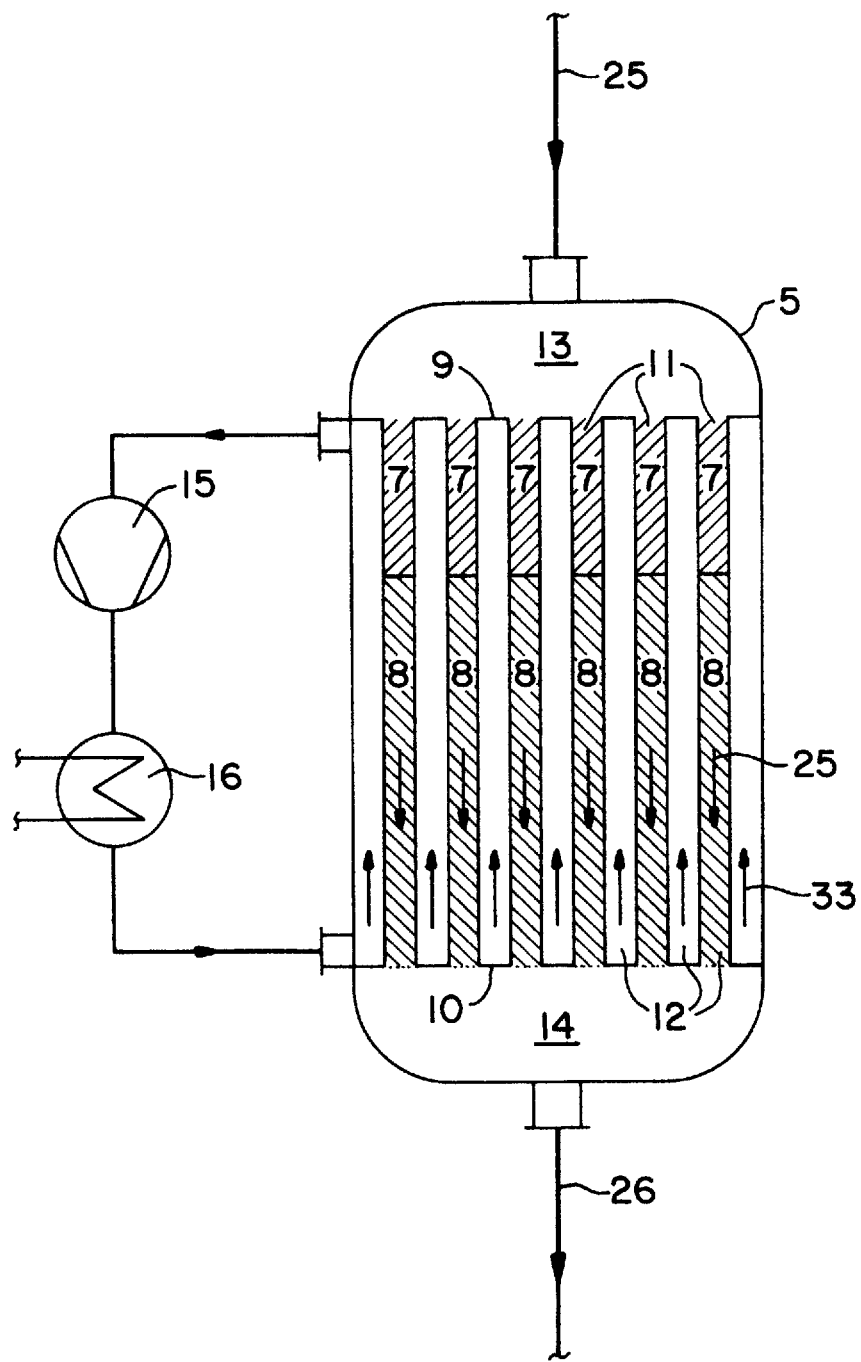
FIG. 2 is a detailed drawing of a multitude reactor with inert and catalyst packing material and circulation of the heat-transfer medium used in accordance with the present invention.

FIGS. 1 and 2 will now be explained in more detail.

FIG. 1 shows a process flow diagram for the first part of methyl mercaptan production, including feed gas pretreatment, reaction in the reactor, and cooling of the product gas mixture.

The reaction in the multitude reactor 5 occurs on a catalyst of aluminum oxide granules charged with 25% by weight cesium tungstate. The particle size of the granules is about 3 mm. This catalyst is described in detail in Example 2 in German Patent Application 196 39 584, which has not yet been published. It can convert a feed gas mixture having a molar ratio of hydrogen sulfide to methanol of 1.5:1 to 2.0:1 to methyl mercaptan at a working pressure of 10 bar, and a reaction temperature between 340° C. and 370° C. when loaded at a spatial velocity, GHSV, of 800 to 1200 hour$^{-1}$, with methanol conversion and selectivity both greater than 90%.

For pretreatment of the feed gas mixture, the hydrogen sulfide make-up gas 20 is compressed to the intermediate pressure of 6 bar in the first stage I of a two-stage screw-type compressor 1, with simultaneous injection of liquid methanol. Part of the methanol is vaporized by the heat of compression, thus limiting the temperature following the first compression stage to a value of about 65° C. The methanol not vaporized by the heat of compression is recycled through the buffer tank 2, and freed of particles flushed out of the compressor by suitable filters. The methanol flow that is vaporized amounts to about 20% to 30% of the methanol required for the reaction at a molar ratio of 1.5:1 to 2.0:1. It is replaced by the flow 21 from another buffer tank 3.

A stream 22 of hydrogen sulfide recycle gas is mixed with the make-up gas which has been compressed to the intermediate pressure. Then this gas mixture is compressed to 11 bar in the second compressor stage II of the screw-type compressor. This final pressure from the screw-type compressor is somewhat greater than the actual working pressure in the reactor, to compensate for piping losses. Because of the heat of compression the temperature of the gas mixture rises to about 100° C. to 110° C.

ASE Methanol vapor 24 is added to the compressed gas stream 23 to establish the desired molar ratio of hydrogen sulfide to methanol. It has a temperature of about 135° C. to 150° C. at a pressure of 11 bar.

The feed gas mixture obtained in this manner is heated in the gas heater 4 to the reactor inlet temperature (preheat temperature) of 150° C. to 200° C. The feed gas mixture enters the reactor 5 at this temperature, where it is heated to the reaction temperature by heat exchange with the reaction heat released in the catalyst bed.

The product gas mixture 26 leaves the reactor at the reaction temperature. Its heat content is utilized to vaporize methanol in heat exchanger 6. In the process, the product gas mixture cools to about 150° C. It is taken as the flow 27 to the second part of the process. The product gas mixture is separated into its components in the second process step of methyl mercaptan production. The separation can be accomplished by various known processes. One particularly advantageous separation of the product gas mixture is described in the parallel patent application, (attorney docket 960182KY, 06-53639).

It is important that the hydrogen sulfide gas separated in the second part of the process be returned as the recycle gas stream 22. The same is true for the methanol not completely consumed in the reactor, which is separated from the product gas mixture, as well as for any wash methanol used in the second part of the process. Both portions of methanol are returned to the buffer tank 3 as flow 28.

Methanol consumed in the production process is replaced by make-up methanol added as a stream 29 from the buffer tank 3.

A stream 30 is taken out of the buffer tank 3 for the methanol wash in the second part of the process, and a stream 31 is taken from buffer tank 3 for the catalytic reaction. The methanol stream 31 is divided into the partial streams 21 and 32. Stream 21 is vaporized in the first compressor stage, and stream 32 is converted to the vapor phase by the hot product gas mixture.

FIG. 2 shows the preferred embodiment of the reactor. The catalyst tubes 11 are welded, parallel to each other, between two tube sheets 9 and 10. The feed gas mixture 25 passes through the distribution head 13 into the catalyst tubes. The catalyst tubes are filled first, in the direction of feed gas flow, with an inert packing 7 of ceramic Raschig rings and then with the catalyst packing 8. After leaving the catalyst tubes, the unreacted gas mixture is collected from collector head 14 as the product gas flow 26 for further processing.

The spaces 12 between the catalyst tubes are filled with a molten salt of potassium nitrate and potassium nitrite (melting point about 150° C.) as the heat-transfer medium 33. The heat-transfer medium is passed through the reactor countercurrently to the feed gases. To do that, the heat-transfer medium is removed from the reactor container below tube sheet 9 and fed back into the intermediate space 12 through an external recycling loop. The circulating pump needed to circulate the heat-transfer medium is indicated as 15.

The heat released in the catalyst packing 8 is transferred to the feed gas in the region of the inert packing 7 by the circulation of the heat-transfer medium. A heat exchanger 16 is provided to heat and cool the heat transfer medium for reactor temperature control.

FIG. 2 shows the preferred orientation of the multi-tube reactor. The tubes are arranged vertically, and the feed gas mixture flows through the reactor from top to bottom. The catalyst tubes have suitable screens at their lower to openings to support the catalyst packing. The reactor can also have any other orientation desired.

The reactor inlet temperature of the feed gas mixture is about 170° C. in steady-state operation. The length of the inert packing is about 15% of the total length of the catalyst. tube to heat the feed gas to the reaction temperature of 360° C. in the inert packing 7.

The product gas flow 26 leaving the reactor has the following typical composition for a molar ratio of 1.8 (hydrogen sulfide/methanol):

Methyl mercaptan 39% by weight
Dimethyl sulfide 1.6% by weight
Dimethyl ether 2.7% by weight
Inert gases ($H_2$, CO, $CO_2$, $N_2$) 2.5% by weight
Water: 15% by weight
Hydrogen sulfide 34% by weight
Methanol 5% by weight The process diagram in FIG. 1 includes the components necessary to carry out the process according to the invention. Other components needed to start up the process are not shown. They include a steam-heated methanol vaporizer which vaporizes the required amount of methanol, in place of the product gas, until the catalytic reaction begins to operate. The heat exchanger 16 is also used to heat up the reactor during this start-up phase. Additional electrical heating can be provided here if necessary.

The process according to the invention is characterized by optimal utilization of the energy flows released in the process. These energy flows are predominantly utilized directly in the same process stage in which they appear. That avoids capital costs of external heat exchangers. For example, part of the methanol required is vaporized by utilizing the heat of compression produced in compression of the hydrogen sulfide make-up gas. The methanol is injected directly into the compressor for that purpose, thus making added cooling for the compressor superfluous.

The feed gas is heated to the reaction temperature directly within the reactor itself using the heat of reaction released at the catalyst bed. An external gas heater is needed only to warm the feed gas mixture to a relatively low reactor inlet temperature, so that it can be appropriately simply designed.

Further variations and modifications of the foregoing will be apparent to those skilled in the art and are intended to be encompassed by the claims appended hereto.

German priority application 196 54 515.3 is relied on and incorporated by reference herein.

We claim:

1. A process for continuous production of methyl mercaptan comprising reacting a feed gas mixture of methanol and hydrogen sulfide in the vapor phase at a reaction temperature between 300° C. and 500° C. and under an operating pressure of 5 to 15 bar in a catalyst bed containing aluminum oxide, the feed gas mixture is obtained through the following process steps:

a) in a first stage of a two-stage compression, sufficiently compressing hydrogen sulfide make-up gas to an intermediate pressure with addition of liquid methanol, thereby generating sufficient heat to vaporize said methanol, b) in a second stage of said two-stage compression mixing recycled hydrogen sulfide gas to the make-up gas to obtain a mixture and compressing the mixture to the operating pressure to obtain a compressed gas mixture, c) adding supplemental methanol in the form of methanol vapor to the compressed gas mixture to produce a feed gas mixture having a molar ratio of hydrogen sulfide to methanol of 1.1 to 3, d) heating the feed gas mixture to a preheat temperature in the range of 150° C. to 200° C., e) further heating of the feed gas mixture to the reaction temperature in heat exchange with the reaction heat released in the catalyst bed, and f) reacting methanol and hydrogen sulfide to produce methyl mercaptan in the catalyst bed.

2. The process according to claim 1, further comprising subsequently separating the methyl mercaptan from the product gas mixture by absorption and distillation, and recycling of unconsumed methanol and hydrogen sulfide, removal of inert gases and wastewater, and replacement of the methanol and hydrogen sulfide consumed.

3. The process according to claim 1, wherein the reaction is carried out in a multi-tube reactor in which the tubes are filled first, in the direction of flow, with an inert packing and then with the catalyst packing, so that the heat of reaction released in the catalyst packing is transferred to the upstream inert packing by a heat-transfer medium circulating between the tubes to heat the feed gas mixture to the reaction temperature.

4. The process according to claim 1, wherein the amount of heat required to vaporize the supplemental methanol is withdrawn from the product gas mixture with simultaneous cooling of the product gas mixture to 100° C. to 150° C.

5. The process according to claim 4, wherein a two-stage screw-type compressor is used in said first stage and liquid methanol is injected directly into said first stage.

6. The process according to claim 5, wherein the liquid methanol is injected in excess and unvaporized methanol is recirculated.

* * * * *